United States Patent
Rosler et al.

(10) Patent No.: US 8,019,551 B2
(45) Date of Patent: *Sep. 13, 2011

(54) BIOLOGICAL DATASET PROFILING OF ASTHMA AND ATOPY

(75) Inventors: Elen S. Rosler, Mountain View, CA (US); Eric J. Kunkel, San Mateo, CA (US); Sylvie Privat, South San Francisco, CA (US); Jennifer Melrose, La Honda, CA (US); Melissa Fischer, Jackson, OR (US); Ellen L. Berg, Palo Alto, CA (US)

(73) Assignee: Bioseek LLC, Burlingame, CA (US)

( * ) Notice: Subject to any disclaimer, the term of this patent is extended or adjusted under 35 U.S.C. 154(b) by 963 days.

This patent is subject to a terminal disclaimer.

(21) Appl. No.: 10/590,751

(22) PCT Filed: Feb. 17, 2005

(86) PCT No.: PCT/US2005/005247
§ 371 (c)(1),
(2), (4) Date: Jun. 27, 2007

(87) PCT Pub. No.: WO2005/093561
PCT Pub. Date: Oct. 6, 2005

(65) Prior Publication Data
US 2008/0020417 A1    Jan. 24, 2008

Related U.S. Application Data

(60) Provisional application No. 60/548,323, filed on Feb. 27, 2004.

(51) Int. Cl.
*G06F 7/00* (2006.01)

(52) U.S. Cl. ............... 702/19; 702/20; 703/11; 707/700
(58) Field of Classification Search .................. None
See application file for complete search history.

(56) References Cited

U.S. PATENT DOCUMENTS

| | | |
|---|---|---|
| 6,656,695 B2 | 12/2003 | Berg |
| 6,763,307 B2 | 7/2004 | Berg |
| 7,266,458 B2 | 9/2007 | Plavec |
| 2004/0063088 A1 | 4/2004 | Berg |
| 2004/0157269 A1 | 8/2004 | Berg |
| 2007/0072246 A1 | 3/2007 | Berg |
| 2007/0087344 A1 | 4/2007 | Plavec |
| 2007/0135997 A1 | 6/2007 | Hytopoulos |

FOREIGN PATENT DOCUMENTS

| | | |
|---|---|---|
| WO | WO01/67103 A1 | 9/2001 |
| WO | WO03/023573 A2 | 3/2003 |
| WO | WO2004/022711 A2 | 3/2004 |
| WO | WO2004/094609 A2 | 11/2004 |
| WO | WO2004/094992 A2 | 11/2004 |
| WO | WO2005/023987 A2 | 3/2005 |

OTHER PUBLICATIONS

Galli et al., "Complexity and redundancy in the pathogenesis of asthma: reassessing the roles of mast cells and T cells", J Exp. Med., 1997, 186(3):343-347.

*Primary Examiner* — Mary Zeman
(74) *Attorney, Agent, or Firm* — Bozicevic, Field & Francis LLP; Pamela J. Sherwood (57) ABSTRACT

Methods and systems for evaluating biological dataset profiles relating to asthma and other atopic conditions are provided, where datasets comprising information for multiple cellular parameters are compared and identified, and used in the evaluation of candidate pharmacologic agents for suitability as therapeutic agents.

5 Claims, 4 Drawing Sheets

BIOLOGICAL DATASET PROFILING OF ASTHMA AND ATOPY

FIELD OF THE INVENTION

The field of the invention is the discrimination between different cellular pathways and their use in the determination of the effect of agents on allergic and atopic conditions, including asthma.

BACKGROUND

Knowledge of the biochemical pathways by which cells detect and respond to stimuli is important for the discovery, development, and correct application of pharmaceutical products. Cellular physiology involves multiple pathways, which have complex relationships. For example, pathways split and join; there are redundancies in performing specific actions; and response to a change in one pathway can modify the activity of another pathway, both within and between cells. In order to understand how a candidate agent is acting and whether it will have the desired effect, the end result, and effect on pathways of interest is as important as knowing the target protein.

BioMAP® methods of analysis for determining the pathways affected by an agent or genotype modification in a cell, and for identifying common modes of operation between agents and genotype modifications, are described in International Patent application WO01/067103. Cells capable of responding to factors, simulating a state of interest are employed. Preferably the cells are primary cells in biologically relevant contexts. A sufficient number of factors are employed to involve a plurality of pathways and a sufficient number of parameters are selected to provide an informative dataset. The data resulting from the assays can be processed to provide robust comparisons between different environments and agents.

Among physiological states of interest are immune disorders. Allergy, or hypersensitivity, of the immune system in its different forms affects more than 20% of the human population. Furthermore, man is a highly susceptible species to anaphylaxis. After sensitization with an allergen, a second exposure elicits constriction of the bronchioles, in some cases resulting in death from asphyxia. This allergic reaction is mediated by allergen-specific antibodies, mostly of the IgE class. The antibodies can be directed against a variety of antigens, such as molecules from pollen, fungi, food, house dust mite, hymenoptera venoms or animal danders. The aggregation of mast cell and basophil high-affinity IgE receptors by IgE and antigen causes the release of mediators and cytokines, including histamine, heparin, eosinophil and neutrophil chemotactic factors, leukotrienes and thromboxanes. While an understanding of the inflammatory process in allergic reactions and asthma has improved remarkably over the past decade; ability to control them remains modest. The prevalence of asthma in industrialized countries has increased by almost 80% since 1980. The specific causes for this increase in prevalence are not clear, but the rise in prevalence may be due in part to the absence of effective therapies that reverse the progression of, or cure, this disease.

It is now generally thought that asthma is a syndrome, typically characterized by the three cardinal features of intermittent and reversible airway obstruction, airway hyperresponsiveness, and airway inflammation, that may arise as a result of interactions between multiple genetic and environmental factors. Nevertheless, most cases of the disorder (the so-called "atopic" or "allergic" asthma) occur in subjects whom also exhibit immediate hypersensitivity responses to defined environmental allergens, and challenge of the airways of these subjects with such allergens can produce reversible airway obstruction. It is also known that the overall incidence of asthma in several different populations exhibits a strong positive correlation with serum concentrations of IgE, which, in humans, is the main Ig isotype that can mediate immediate hypersensitivity responses.

Mast cells, derivatives of hematopoietic precursor cells that undergo their terminal stages of differentiation/maturation in the peripheral tissues in which they reside, express cell surface receptors (FcRI) that permit them to bind the Fc portion of IgE with high affinity. Such IgE-sensitized mast cells, upon encounter with specific antigen that is recognized by their FcRI-bound IgE, secrete a broad panel of bioactive mediators, including: preformed mediators that are stored in the cell's cytoplasmic granules, e.g. histamine, heparin, and neutral proteases, newly synthesized lipid products, e.g. prostaglandin D2 and leukotriene C4, and diverse cytokines. Many of these potentially mast cell-derived mediators can promote reversible airway obstruction, bronchial hyperreactivity, and/or airway inflammation.

However, additional cell types, including eosinophils and Th2 lymphocytes, both of which are well represented in the chronic inflammatory infiltrates in the airways of patients with asthma, also can produce cytokines or other mediators that may contribute to many of the features of the disease. The FcRI, which was once thought to be restricted to tissue mast cells and basophils, is also expressed on the surface of monocytes, circulating dendritic cells, Langerhans' cells, and eosinophils, thus implicating these cells as additional potential sources of mediators in various IgE-dependent inflammatory responses. (For a review, see Galli (1997) J.E.M. 186:343-347, which disclosure and the references cited therein are herein incorporated by reference)

Current evidence supports a complex view of the pathogenesis of allergic diseases, in which both T cells and mast cells (and other FcRI$^+$ cells) can have both effector cell and immunoregulatory roles in these disorders. This indicates that therapeutic approaches for asthma and other allergic diseases must consider the effect on multiple systems. For example, anti-IgE-based strategies not only may reduce CD23-dependent antigen presentation and FcRI$^+$ cell effector function, but also may diminish FcRI$^+$ cell immunoregulatory function by reducing both mast cell (or basophil) IL-4/IL-13 production and FcRI$^+$-dependent antigen presentation. Conversely, the findings that corticosteroids and other immunosuppressive drugs can diminish mast cell cytokine production, as well as reduce IgE- and mast cell-dependent inflammation and leukocyte recruitment in vivo, raise the possibility that the clinical benefits of such agents in asthma may reflect, at least in part, actions on mast cells as well as on the T cells, eosinophils, and other effector and target cells that participate in these complex disorders.

Given the large number of cells and pathways involved in the development of atopic disease, the evaluation of therapeutic modalities requires a complex assessment of effectiveness in multiple systems. The present invention addresses these issues.

SUMMARY OF THE INVENTION

The present invention provides methods and systems for evaluating biological dataset profiles relating to asthma and other atopic conditions, where datasets comprising information for multiple cellular parameters are compared and identified, and used in the evaluation of candidate pharmacologic agents for suitability as therapeutic agents. A typical dataset comprises readouts from multiple cellular parameters resulting from exposure of cells to biological factors in the absence or presence of a candidate agent, where the agent may be a chemical agent, e.g. drug candidate; or genetic agent, e.g. expressed coding sequence. Datasets may include control datasets, and/or profile datasets that reflect the parameter changes of known agents. Known agents may include those having acceptable therapeutic activities against asthma and atopic disease, as well as those exemplifying undesirable side effects. For analysis of multiple context-defined systems, the output data from multiple systems may be concatenated.

In one embodiment of the invention, the biological dataset profile includes one or more asthma associated cell systems. Cells associated with asthma include mast cells; smooth muscle cells, bronchial epithelial cells, T cells, endothelial cells, and the like.

BRIEF DESCRIPTION OF THE DRAWING

FIG. 1A. Regulation of readout parameters on IL-4 stimulated HUVEC in the presence or absence of histamine (10 µM) and/or TNF (5 ng/ml). FIG. 1B. Regulation of readout parameters on IL-4 stimulated HUVEC and HUVEC/MC cocultures in the presence or absence A23187. FIG. 1C. Comparison of effect of MC derivation methods on induction of VCAM expression in HUVEC/MC cocultures. FIG. 1D. Comparison of MC stimulation methods (A23187 or anti-IgE) on induction of VCAM expression in HUVEC/MC cocultures. FIG. 1E. Comparison of effect of UCB donors on induction of VCAM expression in HUVEC/MC cocultures. Multiple derivations of MC from UCB show similar ability to release mediators as determined by the changes in VCAM-1 expression. $p<0.05=*$, $p<0.005=**$.

DETAILED DESCRIPTION OF EMBODIMENTS

The inventive methods and compositions provide a system for the assessment of candidate therapies for atopic diseases, including asthma. Atopic diseases are complex traits that develop as a result of environmentally induced immune responses in genetically predisposed individuals. Atopic disease is manifested by allergic inflammation in the respiratory tract, skin or gastrointestinal tract, as well as by elevated serum IgE, eosinophilia and the symptoms of wheezing, sneezing or hives. In addition, allergic inflammatory responses are characterized by the presence of Th2 lymphocytes producing high levels of IL-4, IL-5, IL-9 and IL-13, which enhance the growth, differentiation and/or recruitment of eosinophils, mast cells, basophils and B cells producing IgE.

Datasets of information are obtained from biologically multiplexed activity profiling (BioMAP®) of agents that are candidates for the treatment or involvement of atopic diseases. Such methods are described, for example, in U.S. Pat. No. 6,656,695; in co-pending U.S. provisional patent application 60/465,152, filed Apr. 23, 2003; in co-pending U.S. provisional patent application 60/539,447, filed Jan. 26, 2004; and U.S. patent applications U.S. Ser. No. 09/952,744, filed Sep. 13, 2001; U.S. Ser. No. 10/220,999; and U.S. Ser. No. 10/236,558, filed Sep. 5, 2002, herein each specifically incorporated by reference. Briefly, the methods provide screening assays for biologically active agents, where the effect of altering the environment of cells in culture is assessed by monitoring multiple output parameters. The result is a dataset that can be analyzed for the effect of an agent on a signaling pathway, for determining the pathways in which an agent acts, for grouping agents that act in a common pathway, for identifying interactions between pathways, and for ordering components of pathways.

Incorporating human biology early in drug development can improve the quality of drug targets and leads and reduce the frequency of compound attrition downstream. Screening methods of interest utilize a systems approach to characterization of drug function based on statistical analysis of protein expression data sets from multiple primary human cell-based disease systems. In these models, biological complexity is provided by the activation of multiple signaling pathways; interactions of multiple primary human cell types; and/or the use of multiple systems for data analysis. These model systems are surprisingly robust, reproducible, and responsive to and discriminatory of the activities of a large number of approved and investigational therapeutic agents.

In order to analyze agents that modulation inflammatory processes, particularly those of relevance to asthma and allergy, model systems containing Th2 T cells, bronchial epithelial cells, primary human mast cells, etc. are used. The multi-cell and/or multifactor design of the systems and their analysis through multi-parameter activity profiles work together to optimize information content, enabling rapid but effective analysis of drug and gene target activities in complex cellular responses relevant to clinical disease.

Allergy, or atopy is an increased tendency to IgE-based sensitivity resulting in production of specific IgE antibody to an immunogen including, for example, insect venom, dust mites, pollens, molds, animal dander, food antigens, or latex. Allergic responses are antigen specific and are characterized by the production of Th2-type cytokines such as, for example, IL-4, IL-5, IL-10, IL-13, etc. Sensitization to a particular allergen occurs in genetically predisposed people after exposure to antigen; cigarette smoke and viral infections may assist in the sensitization process.

Included in the group of individuals suffering from atopy are those with asthma associated allergies. About 40% of the population is atopic, and about half of this group develops clinical disease ranging from trivial rhinitis to life-threatening asthma. After sensitization, continuing exposure to allergens leads to a significant increase in the prevalence of asthma. Ninety percent of children and 80% of adults with asthma are atopic. Once sensitization has occurred, re-exposure to allergen is a risk factor for exacerbation of asthma. Effective management of allergic asthma has typically required pharmacologic therapy and allergen avoidance. The specific physiological effects of asthma associated with allergies include airway inflammation, eosinophilia and mucus production, and production of IL-4 and antigen-specific IgE.

Allergens are immunogenic compounds that cause Th2-type T cell responses and IgE B cell responses in susceptible individuals. Allergens include antigens found in foods such as fruits (e.g., melons, strawberries, pineapple and other tropical fruits), peanuts, peanut oil, other nuts, milk proteins, egg whites, shellfish, tomatoes, etc.; airborne antigens such as grass pollens, animal danders, house mite feces, etc.; drug antigens such as penicillins and related antibiotics, sulfa drugs, barbituates, anticonvulsants, insulin preparations (particularly from animal sources of insulin), local anesthetics (e.g., Novocain), and iodine (found in many X-ray contrast dyes); insect venoms and agents responsible for allergic dermatitis caused by blood sucking arthropods such as Diptera, including mosquitos (*Anopheles* sp., *Aedes* sp., *Culiseta* sp., *Culex* sp.), flies (*Phlebotomus* sp., *Culicoides* sp.) particularly black flies, deer flies and biting midges, ticks (*Dermmacenter* sp., *Ornithodoros* sp., *Otobius* sp.), fleas (e.g., the order Siphonaptera, including the genera *Xenopsylla, Pulex* and *Ctenocephalides felis* felis); and latex. The specific allergen may be any type of chemical compound such as, for example, a polysaccharide, a fatty acid moiety, a protein, etc. Antigen preparations may be prepared by any available technique including, for example, isolation from natural sources, in vivo or in vitro expression of recombinant DNA molecules (see, for example, Zeiler et al. (1997) *J. Allergy Clin. Immunol.* 100(6 Pt 1):721-727, chemical synthesis, or other technique known in the art.

Anaphylactic allergens are those antigens that pose a risk of anaphylactic reaction in hypersensitive individuals. Anaphylaxis is an acute, systemic allergic reaction that occurs after an individual has become sensitized to an antigen. Anaphylaxis is associated with the production of high levels of IgE antibodies and with the release of histamines, which cause muscle contractions, constriction of the airways, and dilation of blood vessels. Symptoms of anaphylactic reactions include hives, generalized itching, nasal congestion, wheezing, difficulty breathing, cough, cyanosis, lightheadedness, dizziness, confusion, slurred speech, rapid pulse, palpitations, nausea and vomiting, abdominal pain or cramping, skin redness or inflammation, nasal flaring, intercostal retractions, etc.

Asthma, as defined herein, is reversible airflow limitation in an individual over a period of time. Asthma is characterized by the presence of cells such as eosinophils, mast cells, basophils, and CD25$^+$ T lymphocytes in the airway walls. There is a close interaction between these cells, because of the activity of cytokines which have a variety of communication and biological effector properties. Chemokines attract cells to the site of inflammation and cytokines activate them, resulting in inflammation and damage to the mucosa. With chronicity of the process, secondary changes occur, such as thickening of basement membranes and fibrosis. The disease is characterized by increased airway hyperresponsiveness to a variety of stimuli, and airway inflammation. A patient diagnosed as asthmatic will generally have multiple indications over time, including wheezing, asthmatic attacks, and a positive response to methacholine challenge, i.e., a PC20 on methacholine challenge of less than about 4 mg/ml. Guidelines for diagnosis may be found, for example, in the *National Asthma Education Program Expert Panel Guidelines for Diagnosis and Management of Asthma*, National Institutes of Health, 1991, Pub. No. 91-3042.

Data Analysis

The data from a typical "system", as used herein, provides a single cell type or combination of cell types (where there are multiple cells present in a well) in an in vitro culture condition. Primary cells are preferred, or in the case of mast cells, cells derived from primary cells, to avoid potential artifacts introduced by cell lines. In a system, the culture conditions provide a common biologically relevant context. Each system comprises a control, e.g. the cells in the absence of the candidate biologically active agent, although usually in the presence of the factors in the biological context. The samples in a system are usually provided in triplicate, and may comprise one, two, three or more triplicate sets.

As used herein, the biological context refers to the exogenous factors added to the culture, which factors stimulate pathways in the cells. Numerous factors are known that induce pathways in responsive cells. By using a combination of factors to provoke a cellular response, one can investigate multiple individual cellular physiological pathways and simulate the physiological response to a change in environment.

Biological contexts of interest for asthma/atopy include primary endothelial cells, which may be provided by primary human umbilical vein endothelial cells (HUVEC); primary microvascular endothelial cells, aortic or arteriolar endothelial cells; etc. Primary endothelial cells respond to a large variety of cellular stimuli. Endothelial cells are highly sensitive to their environment, and they contain a large number of signaling pathways. This provides an opportunity to evaluate the effect of compounds on many pathways and/or pathway interactions. Endothelial cells participate in many disease processes. In inflammation, they control the migration and localization of effector leukocytes and lymphocytes. Among the factors useful for stimulating endothelial cells for these purposes are IL-4 (20 ng/ml); histamine; TNF-α; IL-1; IFNγ; IL-13; TGFβ; mast cell tryptase; fibronectin; etc., which may be used in combinations of one, two, three, four or more factors. Endothelial cells may also be used in a coculture with the cells listed below.

T cells may be used, including Th2 type T cells, and particularly human T cells. T cell sources of interest include peripheral blood mononuclear cell preparations, which may be unselected, thereby providing a complex mixture of myeloid and lymphocytic cells, or may be selected for expression of T cell markers, such CD4$^+$, CD3$^+$; etc. A chronic Th2 assay combination can be defined by the culture of HUVEC with TNF-α and/or IL-1 and IL-4 for 24 hours. Inflammation in chronic Th2 environments, such as asthma, is characterized by the presence of TNF-α, IL-1 and IL-4, but not IFN-γ. Lymphokine-producing activated lymphocytes (CD45RO+, CD44hi, etc.) are a hallmark of inflammatory diseases such as asthma. Depending on the disease environment and tissue site, activated lymphocytes can differ in their expression and function of adhesion molecules and other receptors, as well as in their production of various cytokines and other factors. The ability to selectively block lymphocyte activation associated with the inflammatory disease without inhibiting or suppressing lymphocyte activation associated with the ability to fight infection and neoplasia is a goal of inflammatory drug therapy. Among the factors useful for stimulating T cells for these purposes are IL-2; superantigens, including SEA, SEB, TSST, etc.; anti-CD3; anti-CD28; PHA; ConA; etc.

Fibroblasts, including neonatal fibroblasts may comprise a system. Fibroblasts may be cultured alone, or in combination with endothelial cells, and/or smooth muscle cells, and/or bronchial epithelial cells. Bronchial epithelial cells may also be used alone. Among the factors useful in this context are included TNF-α; IFNβ; IFNγ; TGFβ; IL-4; IL-13; PDGF; FGF; histamine; etc.

The present invention can be applied to the identification of compounds that inhibit or alter mast cell activation. Such compounds have utility in the treatment of allergy and asthma, where mast cell products mediate disease pathology. Mast cells display altered responses depending on their environment. The ability of mast cells to produce IL-3 and GM-CSF is significantly increased in the presence of fibronectin or vitronectin. Mast cells in allergen-induced late-phase cutaneous reactions in atopic patients express high levels of the high affinity IgE receptor compared with mast cells in control skin. Biological contexts including at least one of fibronectin and vitronectin reflect physiologic or disease environments.

Mast cells may be isolated from primary sources, but are preferably generated from progenitor cells in vitro. Myeloid progenitor cells useful for such purposes are well-known in the art, and include $CD34^+$ cells from bone marrow, cord blood, mobilized stem cell populations, and the like. The progenitor cells are cultured by methods known in the art, e.g. in the presence of stem cell factor (SCF) and IL-6. Other supplements for derivation of mast cells may include IL-9, IL-10, TPO, FLT-3L, PGE-2, IL-3 and human IgE. Factors useful in stimulating mast cells include IL-4; anti-IgE; A23187; Compound 48/80; Con A; NP-BSA; etc.

A BioMAP dataset comprises values obtained by measuring parameters or markers of the cells in a system. Each dataset will therefore comprise parameter output from a defined cell type(s) and biological context, and will include a system control. As described above, each sample, e.g. candidate agent, genetic construct, etc., will generally have triplicate data points; and may be multiple triplicate sets. Datasets from multiple systems may be concatenated to enhance sensitivity, as relationships in pathways are strongly context-dependent. It is found that concatenating multiple datasets by simultaneous analysis of 2, 3, 4 or more systems will provide for enhance sensitivity of the analysis.

By referring to a BioMAP is intended that the dataset will comprise values of the levels of at least two sets of parameters, preferably at least three parameters, more preferably 4 parameters, and may comprise five, six or more parameters.

In many cases the literature has sufficient information to establish the system conditions to provide a useful BioMAP. Where the information is not available, by using the procedures described in the literature for identifying markers for diseases, using subtraction libraries, microarrays for RNA transcription comparisons, proteomic or immunologic comparisons, between normal and cells in the physiologic state of interest, using knock-out and knock-in animal models, using model animals that simulate the physiological state, by introducing cells or tissue from one species into a different species that can accept the foreign cells or tissue, e.g. immunocompromised host, one can ascertain the endogenous factors associated with the physiologic state and the markers that are produced by the cells associated with the physiologic state.

The parameters may be optimized by obtaining a system dataset, and using pattern recognition algorithms and statistical analyses to compare and contrast different parameter sets. Parameters are selected that provide a dataset that discriminates between changes in the environment of the cell culture known to have different modes of action, i.e. the BioMAP is similar for agents with a common mode of action, and different for agents with a different mode of action. The optimization process allows the identification and selection of a minimal set of parameters, each of which provides a robust readout, and that together provide a BioMAP that enables discrimination of different modes of action of stimuli or agents. The iterative process focuses on optimizing the assay combinations and readout parameters to maximize efficiency and the number of signaling pathways and/or functionally different cell states produced in the assay configurations that can be identified and distinguished, while at the same time minimizing the number of parameters or assay combinations required for such discrimination. Optimal parameters are robust and reproducible and selected by their regulation by individual factors and combinations of factors.

Parameters are quantifiable components of cells. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc.

Markers are selected to serve as parameters based on the following criteria, where any parameter need not have all of the criteria: the parameter is modulated in the physiological condition that one is simulating with the assay combination; the parameter has a robust response that can be easily detected and differentiated; the parameter is not co-regulated with another parameter, so as to be redundant in the information provided; and in some instances, changes in the parameter are indicative of toxicity leading to cell death. The set of parameters selected is sufficiently large to allow distinction between datasets, while sufficiently selective to fulfill computational requirements.

Parameters of interest include detection of cytoplasmic, cell surface or secreted biomolecules, frequently biopolymers, e.g. polypeptides, polysaccharides, polynucleotides, lipids, etc. Cell surface and secreted molecules are a preferred parameter type as these mediate cell communication and cell effector responses and can be readily assayed. In one embodiment, parameters include specific epitopes. Epitopes are frequently identified using specific monoclonal antibodies or receptor probes. In some cases the molecular entities comprising the epitope are from two or more substances and comprise a defined structure; examples include combinatorially determined epitopes associated with heterodimeric integrins. A parameter may be detection of a specifically modified protein or oligosaccharide, e.g. a phosphorylated protein, such as a STAT transcriptional protein; or sulfated oligosaccharide, or such as the carbohydrate structure Sialyl Lewis x, a selectin ligand. The presence of the active conformation of a receptor may comprise one parameter while an inactive conformation of a receptor may comprise another, e.g. the active and inactive forms of heterodimeric integrin $\alpha_M\beta_2$ or Mac-1.

Parameters of interest for the evaluation of asthma include, without limitation, ACE (CD143); alpha5beta1; alpha-smooth muscle actin; B7-H1; B7-H2; CCR2; CCR3; CCR4; CCR5; CCR6; CCR7; CCR9; CD106; CD117; CD119; CD11c; CD134; CD137; CD150; CD200; CD26; CD30; CD31; CD38; CD40; CD55; CD59; CD62E; CD62P; CD69; CD87; CD87; CD90; CD154; Collagen I; Collagen III; CTLA-4 (CD152); cutaneous lymphocyte antigen (CLA); CXCR3; CXCR4; CXCR5; Elafin/SKALP; Endothelin-1; Eotaxin-2; Eotaxin 3; Eotaxin-1; Ephrin A2; E-Selectin; FasL (CD178); FGF; FGF receptor; GM-CSF; Gro-a; Histamine; HLA-DR; ICAM-1; IFN-γ; IL10; IL-13; IL-16; IL-1α; IL-2; IL-4; IL-4Ralpha; IL-5; IL-6; IL-8; IL-9; integrin a5b1; IP-10; I-TAC; Keratin 8/18; LDL receptor; L-selectin (CD62L); LT-alpha; mast cell tryptase; MCP-1; MCP-4 and MIP-3a; m-CSF; MIG; MMP1; MMP-13; MMP2; MMP2;

MMP-9; MMP-9; MMP-9; OX40 (CD134); PAI-1; PAR2; PDGF; P-selectin; Tarc; TGF-β; thrombomodulin; TIMP-2; tissue factor (CD142); TNF-alpha; uPA; uPAR (CD87); VCAM-1; VEGFR2; etc.

Candidate biologically active agents may encompass numerous chemical classes, primarily organic molecules, which may include organometallic molecules, inorganic molecules, genetic sequences, etc. An important aspect of the invention is to evaluate candidate drugs, select therapeutic antibodies and protein-based therapeutics, with preferred biological response functions. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetic agents, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

The term "genetic agent" refers to polynucleotides and analogs thereof, which agents are tested in the screening assays of the invention by addition of the genetic agent to a cell. Genetic agents may be used as a factor, e.g. where the agent provides for expression of a factor. Genetic agents may also be screened, in a manner analogous to chemical agents. The introduction of the genetic agent results in an alteration of the total genetic composition of the cell. Genetic agents such as DNA can result in an experimentally introduced change in the genome of a cell, generally through the integration of the sequence into a chromosome. Genetic changes can also be transient, where the exogenous sequence is not integrated but is maintained as an episomal agents. Genetic agents, such as antisense oligonucleotides, can also affect the expression of proteins without changing the cell's genotype, by interfering with the transcription or translation of mRNA. The effect of a genetic agent is to increase or decrease expression of one or more gene products in the cell.

Agents are screened for biological activity by adding the agent to cells in the system; and may be added to cells in multiple systems. The change in parameter readout in response to the agent is measured to provide the BioMAP dataset.

The data, particularly data from multiple asthma relevant systems, may be subjected to non-supervised hierarchical clustering to reveal relationships among profiles. For example, hierarchical clustering may be performed, where the Pearson correlation is employed as the clustering metric. Clustering of the correlation matrix, e.g. using multidimensional scaling, enhances the visualization of function homology similarities and dissimilarities. Multidimensional scaling (MDS) can be applied in one, two or three dimensions. Application of MDS produces a unique ordering for the agents, based on the distance of the agent profiles on a line. To allow objective evaluation of the significance of all relationships between compound activities, profile data from all multiple systems may be concatenated; and the multi-system data compared to each other by pairwise Pearson correlation. The relationships implied by these correlations may then be visualized by using multidimensional scaling to represent them in two or three dimensions.

Biological datasets are analyzed to determine statistically significant matches between datasets, usually between test datasets and control, or profile datasets. Comparisons may be made between two or more datasets, where a typical dataset comprises readouts from multiple cellular parameters resulting from exposure of cells to biological factors in the absence or presence of a candidate agent, where the agent may be a genetic agent, e.g. expressed coding sequence; or a chemical agent, e.g. drug candidate.

A prediction envelope is generated from the repeats of the control profiles; which prediction envelope provides upper and lower limits for experimental variation in parameter values. The prediction envelope(s) may be stored in a computer database for retrieval by a user, e.g. in a comparison with a test dataset.

In one embodiment of the invention, the analysis methods provided herein are used in the determination of function homology between two agents. As used herein, the term "function homology" refers to determination of a similarity of function between two candidate agents, e.g. where the agents act on the same target protein, or affect the same pathway. Function homology may also distinguish compounds by the effect on secondary pathways, i.e. side effects. In this manner, compounds or genes that are structurally dissimilar may be related with respect to their physiological function. Parallel analyses allow identification of compounds with statistically similar functions across systems tested, demonstrating related pathway or molecular targets. Multisystem analysis can also reveal similarity of functional responses induced by mechanistically distinct drugs.

Classes of agents acting in asthma associated contexts include anti-histamines, corticosteroids, beta-agonists, bronchodilators, anti-cholinergics, leukotriene modifiers, IgE antagonists, and mast cell stabilizers (e.g. cromolyn). Compounds in these classes may be used to generate known profiles for activity. Additionally, compounds in these classes may be tested for therapeutic profiles in the assays of the present invention, e.g. where derivatives and analogs of known agents are tested for activity; agents sharing common structural features with known agents in these classes, and the like.

EXAMPLES

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental, errors and deviations should be allowed for. Unless otherwise indicated, parts are parts by weight, molecular weight is weight average molecular weight, temperature is in degrees centigrade; and pressure is at or near atmospheric.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. It is particularly to be understood that the present invention is not limited to the particular embodiments described herein. For example, the invention is not restricted to the particular methodology, protocols, cell lines, animal species or genera, constructs and reagents described herein as such may vary. The foregoing has been merely a description of certain preferred embodiments of the invention, not intended to limit the scope of that invention, which is defined only by the appended claims.

Example 1

Regulators of Endothelial Cell Responses to Allergic Inflammation (HUVEC—IL4/HIS)

The present invention is applied for the screening of compounds for use in treating allergic inflammatory responses such as allergy, asthma, atopic dermatitis and chronic inflammatory diseases disposed towards a Th2 phenotype or modulation of Th2 type immune responses.

Primary human umbilical vein endothelial cells (HUVEC) are used. Other cells that may replace HUVEC in the screen include primary microvascular endothelial cells, aortic or arteriolar endothelial cells. $2-10\times10^4$ cells/ml are cultured to confluence in EGM-2 (Clonetics). Other media that may replace EGM-2 include EGM (Clonetics) and Ham's F12K medium supplemented with 0.1 mg/ml heparin and 0.03-0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745, 1973; Hoshi, PNAS 81:6413, 1984).

The following are then applied for 24 hours: IL-4 (5 ng/ml), and histamine (HIS) (10 µM). In subsequent panels one or more of TNF-α (5 ng/ml), IL-1 (1 ng/ml), IFNγ, (20-100 ng/ml) IL-13 (20 ng/ml), TGFbeta (20 ng/ml), mast cell tryptase, or fibronectin are added to the initial two factors or may replace one of the factors. Standard concentrations of agents are employed as described in the literature. Based on the parameters altered by the indicated factors, BioMAPs are generated for the parameters CD55, VCAM-1, P-selectin, Eotaxin-3, MCP-1, VEGF receptor 2 and uPAR (CD87). Other markers of interest for adding to the BioMAP include: ACE (CD143), a5b1, CD31, Endothelin-1, Ephrin A2, IL-6, LDL receptor, MMP1, MMP2, PAI-1, Eotaxin-1-2, HLA-DR, MIG, TARC, thrombomodulin, Collagen I, III, IV, and tissue factor (CD142).

Example 2

Regulators of T Cell Function—Th2 Responses HUVEC/Th2-Sag/IL2

The present invention is applied for the screening of compounds that inhibit the activation of Th2 lymphocytes.

Human peripheral blood CD4$^+$ T cells are employed. Other cells that may be employed include human peripheral blood CD3$^+$ cells. Cells are isolated from human peripheral blood mononuclear cells utilizing Ficoll-hypaque density gradient centrifugation as described (Ponath, JEM 183:2437, 1996). Following adherence of cells to plastic, CD4$^+$ cells are isolated from non-adherent cells using Miltenyi magnetic beads as described (Andrew, J I 166:103, 2001) or isolated by negative selection using MACS beads as described (Kim, JCI 108:1331, 2001). Purified CD4+ lymphocytes are then cultured 6-7 days at $0.5\times10^6$ cells/ml in complete RPMI (RPMI-1640+50 µg/50 U penicillin/streptomycin+10% FCS+50 µM beta-mercaptoethanol+1 mM sodium pyruvate+2 mM L-glutamine) in plates precoated 12 hr with 1-5 µg/ml anti-CD3 (Pharmingen).

To these cultured T cells is added 1 µg/ml anti-CD28 antibody (Pharmingen) for costimulation and 5 ng/ml IL-2 for growth. Other reagents that can be substituted for co-stimulation include, but are not limited to, anti-CD49d, anti-CD2, or CD40-Ig at effective concentrations. In addition, cytokines important for the differentiation of the T cells are added in particular combinations along with antibodies against other cytokines to induce differentiation and polarization. Usual combinations include 10 ng/ml IL-4, 3 µg/ml anti-IL-12, 3 µg/ml anti-IFN-gamma to mimic TH2 polarization conditions. In subsequent experiments, 10 ng/ml of IL-13, IL-6, or IL-9 may be added to the TH2 condition. After 6-7 days, the same population of T cells is split and restimulated in the same manner as described above, and the cells can be stimultated for more 6-7 day cycles for further polarization. Cells are harvested and resuspended to $10^5$ cells/ml and added to confluent endothelial cells.

Primary human umbilical vein endothelial cells (HUVEC) are used. Other cells that may replace HUVEC in the screen include primary microvascular endothelial cells, aortic or arteriolar endothelial cells. $2-10\times10^4$ cells/ml are cultured to confluence in EGM-2 (Clonetics). Other media that may replace EGM-2 include EGM (Clonetics) and Ham's F12K medium supplemented with 0.1 mg/ml heparin and 0.03-0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745, 1973; Hoshi, PNAS 81:6413, 1984).

Following addition of Th2 cells to endothelial cells, the following are applied: IL-2 (2 ng/ml) and superantigen (SEB, 2 ng/ml+TSST, 2 ng/ml), in the presence of test agent or buffer control. Other stimuli that may replace IL-2 or superantigens include: anti-CD3 (1 µg/ml), anti-CD28 (10 µg/ml), PHA (1 µg/ml) and ConA.

Based on the parameters altered by the indicated factors, BioMAPs are generated for the parameters IFN-γ, TNF-alpha, IL-2, IL-4, IL-5, IL-8, MO, IL-13, LT-alpha, CCR4, CCR5, CXCR3, IL-4Ralpha, CD11c, CD38, CD40, CD69, E-Selectin, Eotaxin-3, CD106, CD134, CD150, CD137, CD69, CD200, B7-H1, B7-H2, MIG and urokinase-type plasminogen activator receptor (uPAR, CD87), Other parameters of interest include alpha4beta7 integrin, L-selectin (CD62L), CD40L, OX40 (CD134), FasL (CD178), CCR3, CCR6, CCR7, CXCR4, CXCR5, CCR9, CCR2, cutaneous lymphocyte antigen (CLA), CTLA-4 (CD152) and CD154, CD26, CD30, Tissue factor, P-selectin ligand activity.

Example 3

Regulators of Fibroblast Responses HDF-3C/TGF, HDF-TGF, HDF-IL4/IL13/TGF

The present invention is applied for the screening of compounds that inhibit fibroblast responses.

Human neonatal fibroblasts (HDFn) are used. Cells are cultured at $3\times10^4$ cells/ml in DMEM/F12 (50/50) from Cellgro, supplemented with LSGS kit (from Cascade Biologics); fetal bovine serum, 2% v/v, hydrocortisone 1 ug/ml, human epidermal growth factor 10 ng/ml, basic fibroblast growth factor 3 ng/ml and heparin 10 µg/ml, and penicillin/streptomycin amphotericin B solution (PSA), until confluency. Medium is replaced with DMEM/F12 with only penicillin/streptomycin amphotericin B solution (PSA), then 24 hours later, the following are applied:

| Factors | Designation |
| --- | --- |
| TNF (5 ng/ml), IL-1 (1 ng/ml), IFN (20 ng/ml) and TGFβ (20 ng/ml) | HDF-3C/TGF |
| TGFβ (20 ng/ml) | HDF-TGF |
| TGFβ (20 ng/ml), IL-4 (20 ng/ml) and IL-13 (20 ng/ml) | HDF-IL4/IL13/TGF |

After another 24 hours incubation (37° C., 5% $CO_2$) the cultures are evaluated for the following parameters: For the HDF3CT system: ICAM, VCAM, CD40, CD90, IP-10, MCP-1, Collagen I, Mig, m-CSF, TIMP-2, PAI-I, and IL-8; for the HDFT system: CD90, Collagen I, Collagen III, HLA-DR, PAI-I, and VCAM; and for the HDF413T system: CD40, CD90, Collagen I, Collagen III, MMP-1, MMP-13, Eotaxin 3, m-CSF, ICAM, TIMP-2, PAI-I, and VCAM.

Example 4

Regulators of Smooth Muscle Responses SMC-3C

The present invention is applied for the screening of compounds that inhibit smooth muscle cell responses.

Primary human umbilical artery smooth muscle cells (UASMC) are used. Other cells that may replace UASMC in the screen include primary aortic, bronchial, coronary artery or pulmonary artery smooth muscle cells. Passage 5-7 cells are used for the screen. $4\times10^4$ cells/ml are cultured to 80% confluence in SmGM-2 (Clonetics) containing 5% FBS. In some cases, SmGM-2 may be removed 24 hours before screen, and replaced with serum-free SmBM basal media (Clonetics) supplemented with insulin.

The following are then applied for 24 hours: Factors include a combination of IL-4 (5 ng/ml), and histamine (HIS) (10 µM) or a combination of IL-1 (1 ng/ml), TNF-α (5 ng/ml) and IFNγ (20 ng/ml). Standard concentrations of agents are employed as described in the literature.

Based on the parameters altered by the indicated factors, BioMAPs are generated for the parameters VCAM, CD40, HLA-DR, ICAM, IL-8, MCP-1, M-CSF, MIG, Thrombomodulin, and uPAR. Other markers of interest include: ACE, alpha5beta1, IP-10, alpha-smooth muscle actin, Collagen I, FGF receptor, IL-6, LDL receptor, MMP1, MMP2, PAI-1 and VEGF receptor II.

Example 5

Regulators of Bronchial Epithelial Cell Responses BREPI3C, BREPITNF413

The present invention is applied for the screening of compounds that inhibit the bronchial epithelial cell responses.

Normal human bronchial epithelial cells are used. Cells are cultured and plated in supplemented BEBM medium % (Cambrex) at $2\times10^4$/ml. Cells may also be cultured with Bronchial/Tracheal Epithelial Cell Serum-Free Growth Medium (Cell Applications, Inc.) or F12/DMEM supplemented with 10 µg/ml rhu-insulin, 10 µg/ml transferrin, 10 ng/ml epidermal growth factor (EGF), 1 µM ethanolamine, 25 µg/ml aprotinin, 25 µg/ml glucose, 1 µM phosphoethanolamine, 5 µM triiodothyronine, 50 nM selenium, 1 nM hydrocortisone, 1 nM progesterone, 5 µM forskolin, 10 µM heregulin β177-244, 5 µl/ml fibronectin, 4 µl/ml bovine pituitary extract and retinoid acid.

Upon reaching confluency, the test agent or buffer control is added and the following are applied: 10 ng/ml of IL-16, 10 ng/ml TNFα and 100 ng/ml IFN-γ (BrEPI3C); 5 ng/ml of IL-4, 10 ng/ml IL-13 and 5 ng/ml TNFα (BrEPITNF413). After another 24 hours incubation (37° C., 5% $CO_2$) the cultures are evaluated for the following parameters: For BrEPI3C: ICAM-1, IL-1a, IP-10, TGF-β, MIG, HLA-DR, PAI-1, I-TAC, MMP-1, MMP-9, CD87 and Keratin 8/18. For BrEPITNF413: Eotaxin-3, ICAM-1, IL-1a, IL-8, TGF-β, PAI-1, MMP-9, uPA and Keratin 8/18. Additional readouts of interest may include CD44, E-cadherin, CD40, EGF-receptor, IL-15Ralpha, CD1d, CD80, CD86, TARC, eotaxin-1, CD95, Elafin/SKALP, Endothelin-1, Gro-a, CD119, IL-6, GM-CSF, IL-16, FGF, PDGF, MCP-4 and MIP-3a.

Example 6

Regulators of Fibroblast/Bronchial Epithelial Cell Responses

The present invention is applied for the screening of compounds that inhibit fibroblast/bronchial epithelial cell responses.

Human neonatal fibroblasts (HDFn) and normal human bronchial epithelial cells (BrEPI) are used. HDFn are cultured in DMEM/F12 (50/50) from Cellgro, supplemented with LSGS kit (from Cascade Biologics); fetal bovine serum, 2% v/v, hydrocortisone 1 µg/ml, human epidermal growth factor 10 ng/ml, basic fibroblast growth factor 3 ng/ml and heparin 10 µg/ml, and penicillin/streptomycin amphotericin B solution (PSA). BrEPI are cultured in supplemented BEBM medium (Cambrex) at $2\times10^4$/ml. BrEPI may also be cultured with Bronchial/Tracheal Epithelial Cell Serum-Free Growth Medium (Cell Applications, Inc.) or F12/DMEM supplemented with 10 µg/ml rhu-insulin, 10 µg/ml transferrin, 10 ng/ml epidermal growth factor (EGF), 1 µM ethanolamine, 25 µg/ml aprotinin, 25 µg/ml glucose, 1 µM phosphoethanolamine, 5 µM triiodothyronine, 50 nM selenium, 1 nM hydrocortisone, 1 nM progesterone, 5 µM forskolin, 10 µM heregulin 11177-244, 5 µl/ml fibronectin, 4 µl/ml bovine pituitary extract and retinoid acid. HDFn are plated for assays at $3\times10^4$ cells/ml. After 2 days, media is replaced with BrEPI media containing $10^4$ BrEPI cells and cultured for a further 2 days.

Upon reaching confluency, the test agent or buffer control is added and the following are applied: 5 ng/ml of IL-4 and 10 ng/ml IL-13 (HDFBrEPI413). After another 24 hours incubation (37° C., 5% $CO_2$) the cultures are evaluated for the following parameters: of CD90, Keratin 8/18, Eotaxin-3, I-TAC, ICAM-1, CD119, IL-1α, IL-8, MCP-1, MMP-9, MMP-1, PAI-1, TGF-β, TIMP-2, uPA, CD87 and VCAM-1. Additional readouts of interest may include ICAM-1, IP-10, Elafin/SKALP, Endothelin-1, Gro-a, CD119, IL-6, GM-CSF, IL-16, FGF, PDGF, CD44, E-cadherin, CD40, EGF-receptor, IL6, IL-15Ralpha, CD1d, CD80, CD86, TARC, eotaxin-1, CD95, MCP-4 and MIP-3a. Other stimuli of interest include: TNFα, TGFbeta, IL-5, IL-10, IL-9, Tryptase, GM-CSF, IL-17, CD40L, Histamine, IgE stimulated Mast Cells and PBMC stimulated with LPS or SAg.

Example 7

Regulators of Mast Cell Responses HUVEC/MC—IgE

The present invention is applied for the screening of compounds that inhibit the mast cell responses. Mast cells profiles are demonstrated to have the ability to modulate the parameter profile of primary endothelial cells by cell-cell interations. Drug profiling in Mast Cell models yields unique profiles and can allow for identification and characterization of mast cell specific compounds. Umbilical cord blood (UCB)-derived mast cells were incorporated in cocultures with primary human endothelial cells in high throughput assay formats. Cocultures respond to mast cell degranulation stimuli, including calcium ionophone (A23183) and IgE cross-linking, by modulating the expression of a number of proteins. Compounds from several different mechanism classes including H1-receptor antagonists, src-family kinase inhibitor, PDE4 inhibitor and mast cell stabilizer had activity in these assays and could be distinguished.

Cryopreserved CD34$^+$ Umbilical Cord Blood (UCB) cells are obtained from AllCells, LLC or Cambrex. CD34$^+$ UBC cells can also be isolated from unfractionated UCB using Miltenyi CD34-isolation kits. CD34$^+$ UCB cells are cultured with 100 ng/ml SCF and 50 ng/ml IL-6 (Peprotech) in Yssel's Media (Gemini) or IMDM (Mediatech) supplemented with 2% FBS or 2% BSA (Sigma) and 1× Pen/Strep (Mediatech), 5 mM 2-ME (Gibco), 1× Insulin/Trasferrin/Selenium A (Gibco), 1 mM Na Pyruvate (Gibco) and 0.1 mM MEM Non-essential Amino Acids (Gibco) or IMDM with 10% FBS. Other supplements for derivation of mast cells may include IL-9, IL-10, TPO, FLT-3L, PGE-2, IL-3 and human IgE. Cells are cultured in 6-well plates. Every 7 days, one half of the media is replaced with fresh media supplemented with IL6 and SCF and non-adherent cells are transferred to the new tissue culture plate, plastic-adherent population is discarded. Volume of media is adjusted as needed to maintain less then a million cells/ml. Cells are cultured under these conditions for 5-15 weeks.

Cells cultured in 10% FBS containing, media become 10-20% mast cells by week 5 and maintain that number of mast cells at least through week 15. Cells cultured in 2% BSA containing media become >80% mast cells and can be utilized for BioMAP assays at week 5 of culture, cells cultured in other media become >80% mast cells and can be utilized for BioMAP assays at week 9-10 of culture. At the end of culture mast cell are induced for 1-2 weeks in media supplemented with 10% FBS and 20 ng/ml IL-4±5 mg/ml human IgE alone or together in combinations. Induced mast cells are incubated with 10 mg/ml human IgE for 2-12 hours at 37° C. prior to addition to the BioMAP assay. IgE-labeled mast cells are seeded into 96-well plates onto confluent HUVEC at 5-20×10$^3$ cells/well in EGM-2 media.

Primary human umbilical vein endothelial cells (HUVEC) are used. Other cells that may replace HUVEC in the screen include primary microvascular endothelial cells, aortic or arteriolar endothelial cells. 2×10$^4$ cells/ml are cultured to confluence in EGM-2 (Clonetics). Other media that may replace EGM-2 include EGM (Clonetics) and Ham's F12K medium supplemented with 0.1 mg/ml heparin and 0.03-0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745, 1973; Hoshi, PNAS 81:6413, 1984).

Test agents or buffer controls are added and mast cells, and cocultures are stimulated with 5 ng/ml IL-4 and 20 mg/ml goat anti-human IgE or 1 mM A23187 (Sigma) or 3 mg/ml Compound 48/80 (Sigma) or NP-BSA (Biosearch Technologies, Inc.) or 5 mg/ml Concavalin A (Sigma) or LPS. After 24 hour, plates are dried and evaluated for expression of mast cell Tryptase, VCAM-1, CD87, CD62P, ICAM-1, IL-8, Eotaxin-3, CD55, VEGFR2, Endothelin-1, PAI-1 and MCP-1. Other markers of interest may include CD142, CD69, CD62E, PAR2, IL-1a, CD59, HLA-DR, CD117, IL-4, IL-5, GM-CSF, fibronectin, vitronectin and IL-6.

Mast cells may also be cocultured with bronchial epithelial cells, HEKn, HDFn and smooth muscle cells to generate BioMAP assays relevant to asthma and allergy states.

Example 8

Multisystem Analysis

Figure 1:
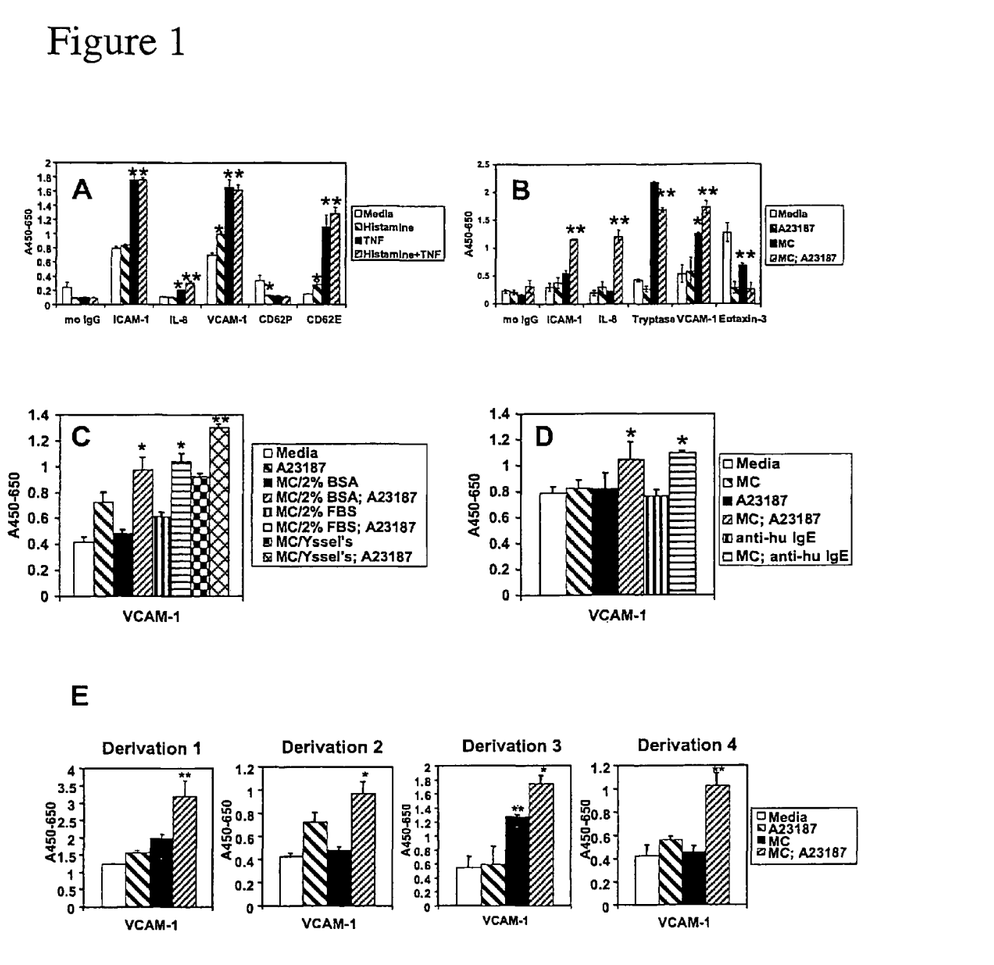
FIG. 1. IL-4-stimulated HUVEC modulate the expression of readout parameters in response to mast cells in coculture, or to mast-cell-derived mediators histamine and TNFalpha. Confluent HUVEC were stimulated with IL-4 in the presence or absence of histamine and/or TNFalpha or $10^4$ cells/well of UCB-derived MC (week 10-11, low- or no-serum conditions), prepared as described in methods in the presence of human IgE. Mast cell/HUVEC cocultures were further stimulated with goat anti-human IgE or A23187. After 24 hour, cultures were evaluated for expression of various markers by cell-based ELISA.

Analysis was performed in multiple systems. IL-4-stimulated HUVEC were evaluated for their responsiveness to mast cells in coculture, or to mast-cell-derived mediators histamine and TNF. Confluent HUVEC monolayers were stimulated with IL-4 in the presence or absence of histamine and/or TNF or 10 cells/well of IgE-labeled UCB-derived MC (week 10-11, low- or no-serum conditions) in multi-well plates. Mast cell/HUVEC cocultures were further stimulated with goat anti-human IgE or A23187. After 24 hour, cultures were evaluated for expression of various markers by cell-based ELISA. FIG. 1A, Expression of markers on IL-4 stimulated HUVEC in the presence or absence of MC mediators, Histamine (10 mM) and TNF (5 ng/ml). FIG. 1B. Expression of markers on IL-4 stimulated HUVEC and HUVEC/MC cocultures in the presence or absence A23187. FIG. 1C Comparison of MC derivation methods on induction of VCAM expression in HUVEC/MC cocultures. FIG. 1D. Comparison of MC stimulation methods on induction of VCAM expression in HUVEC/MC cocultures. FIG. 1E. Comparison of UCB donors on induction of VCAM expression in HUVEC/MC cocultures. Multiple derivations of MC from UCB have show very similar ability to release mediators as determined by the changes in the HUVEC marker expression.

Figure 2:
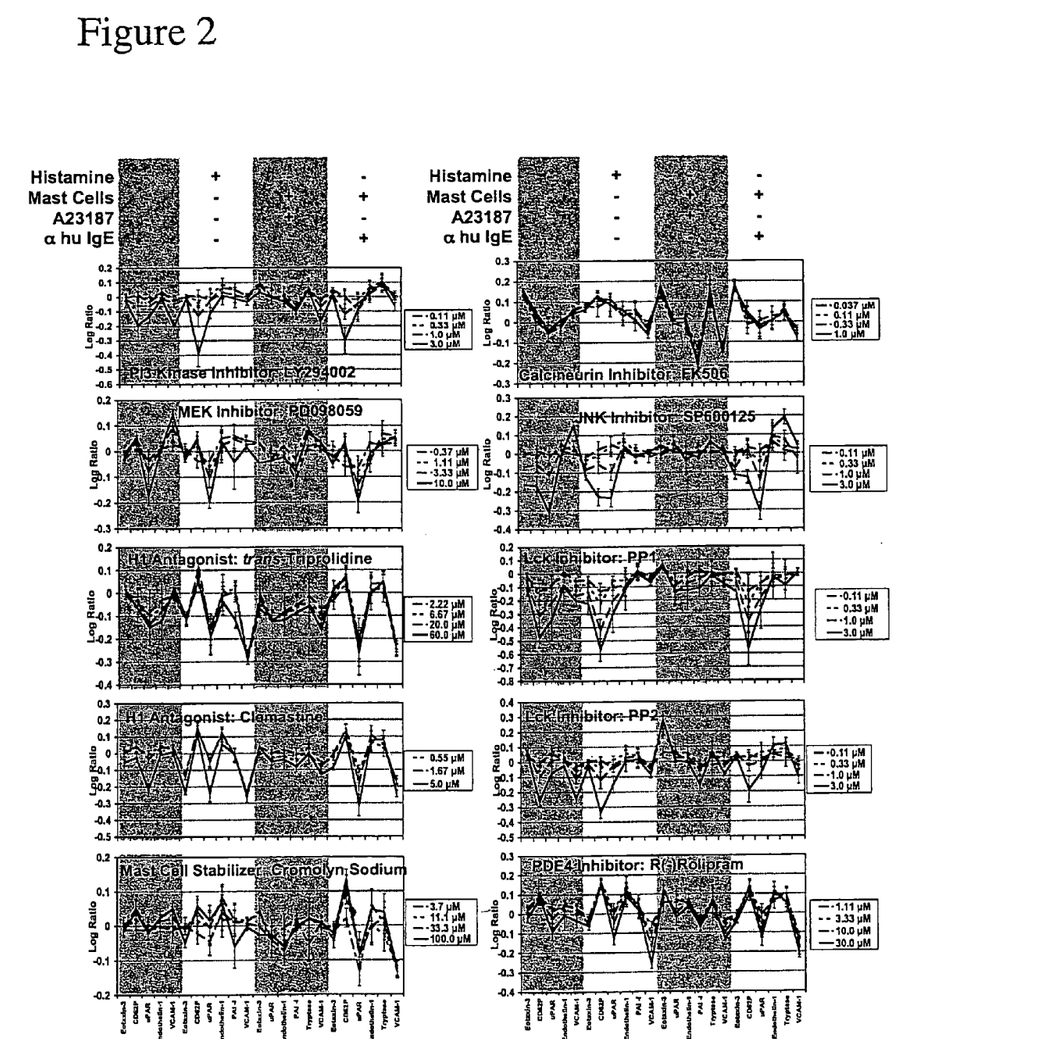
FIG. 2. BioMAP response profiles for several compounds tested in four model systems.

Profiles for several compounds tested in HUVEC/IL-4 BioMAP® model system. As shown in FIG. 2, HU/IL-4, HU/IL-4/His, HU/MC/IL4/A23187 and HU/MC/IL4/IgE model systems were concatenated for analysis. Mast cells (MC) were derived from CD34+ UCB cells in low/no-serum conditions. At week 10, MC were cultured for 7 days with IL-4 and 10% FBS, and treated with human IgE prior to initiation of BioMAP assays. Compounds (or control buffers) and factors were added to HUVEC or HUVEC+MC for 24 hours then readout parameters were measured by ELISA. Systems included HUVEC+IL-4, HUVEC+IL-4+Histamine, HUVEC+IL-4+104 MC+A23187 and HUVEC+IL-4+104 MC+goat anti human IgE. The ordinate shows the log expression ratio [log 10(parameter value with compound/parameter value with solvent control)]. Individual readouts are shown along the abscissa. Compounds were tested at the indicated concentrations.

Figure 3:
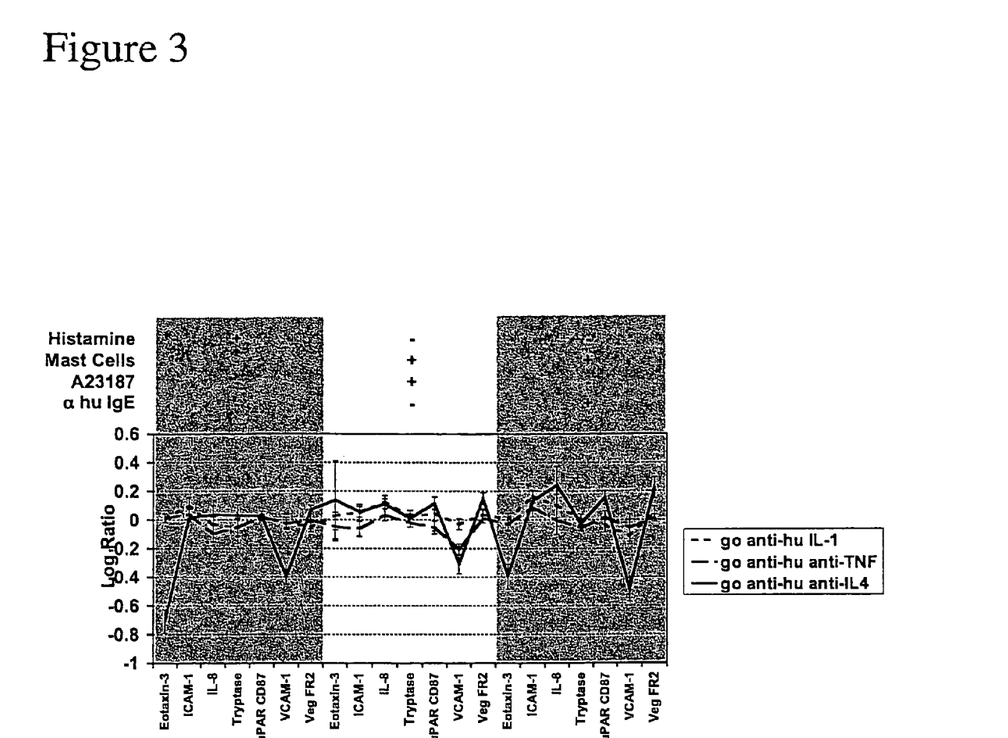
FIG. 3. BioMAP response profiles for blocking antibodies tested in three model systems.

Shown in FIG. 3 is analysis with the HU/IL-4/His, HU/MC/IL4/A23187 and HU/MC/IL4/IgE model systems. Assays were performed as in FIG. 2 in the presence of 2 µg/ml blocking antibodies to IL-1 beta (goat anti-hu IL-1), TNFalpha (goat anti-hu TNF) or IL-4 (goat anti-hu-IL-4) or controls. The ordinate shows the log expression ratio [$\log_{10}$(parameter value with compound/parameter value with solvent control)]. A representative experiment is shown, average of 3 samples+/−standard deviation. Individual readouts are shown along the abscissa.

Figure 4:
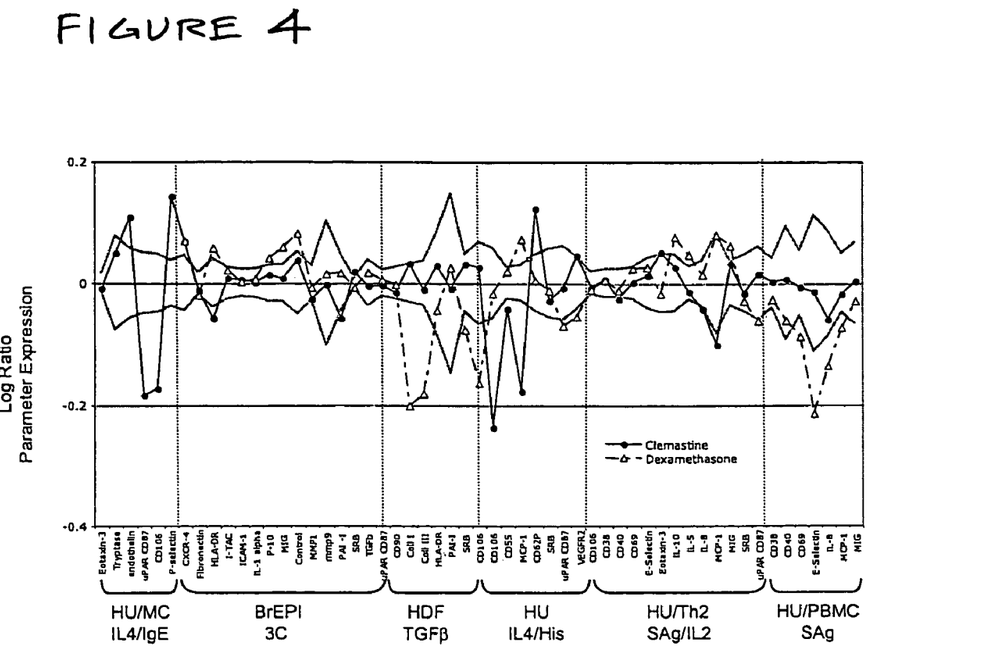
FIG. 4. BioMAP response profiles for Clemastine, an H1 receptor antagonist, and dexamethasone, a glucocorticoid, tested in 6 model systems.

Shown in FIG. 4 is analysis with HU/MC/IL4/IgE, BrEPI/3C, HDF/TGFbeta, HU/IL4/His, HU/Th2/SAg/IL2, and HU/PBMC/SAg. Assays were performed as described in the presence of 550 nM clemastine, 10 microM dexamethasone or solvent controls. The ordinate shows the log expression ratio [$\log_{10}$(parameter value with compound/parameter value with solvent control)]. Representative experiments are shown, average of 3-9 samples. The solid grey lines indicate the 99% confidence limits calculated from solvent controls. Individual readouts are shown along the abscissa. HU/MC/IL4/IgE system parameters included Eotaxin-3, mast cell-specific Tryptase, Endothelin-1, uPAR/CD87, CD106 and P-selectin. BrEPI3C system parameters included CXCR-4, Fibronectin, HLA-DR, I-TAC, ICAM-1, IL-1alpha, IP-10 (P-10), MIG, MMP1, MMP9, PAI-1, SRB, TGFbeta, and uPAR/CD87. HDF/TGFbeta system parameters included CD90, Collagen I, Collagen III, HLA-DR, PAI-1, SRB and CD106. HU/IL4/His system parameters included CD106, CD55, MCP-1, CD62P, Resazurin, SRB, uPAR/CD87 and VEGFR2. HU/TH2/SAg/IL2 system parameters included CD106, CD38, CD40, CD69, E-selectin, Eotaxin-3, IL-10, IL-5, IL-8, MCP-1, MIG, SRB and uPAR/CD87. HU/PBMC/SAg system parameters included CD38, CD40, CD69, E-selectin, IL-8, MCP-1 and MIG.

What is claimed is:

1. A method for characterization of a candidate agent according to its effect on allergic/atopic conditions, the method comprising:
    contacting said candidate agent with an asthma/atopy context system selected from
    (a) primary human umbilical vein endothelial cells (HUVEC) in the presence of IL-4 and histamine with at least three different cellular parameters selected from CD55, VCAM-1, P-selectin, Eotaxin-3, MCP-1, VEGF receptor 2 and uPAR (CD87);
    (b) HUVEC and T cells in the presence of IL-2 and superantigen with at least three different parameters selected from IFN-γ, TNF-alpha, IL-2, IL-4, IL-5, IL-8, IL10, IL-13, LT-alpha, CCR4, CCR5, CXCR3, IL-4Ralpha, CD11c, CD38, CD40, CD69, E-Selectin, Eotaxin-3, CD106, CD134, CD150, CD137, CD69, CD200, B7-H1, B7-H2, MIG and CD87;
    (c) Human neonatal fibroblasts (HDFn) in the presence of TNF, IL-1, IFN and TGFβ with at least three different parameters selected from ICAM, VCAM, CD40, CD90, IP-10, MCP-1, Collagen I, Mig, m-CSF, TIMP-2, PAI-I, and IL-8
    (d) HDFn in the presence of TGFβ with at least three different parameters selected from CD90, Collagen I, Collagen III, HLA-DR, PAI-I, and VCAM
    (e) human bronchial epithelial cells and HDFn in the presence of IL-4 and TNFα with at least three different parameters selected from ICAM-1, IL-1a, IP-10, TGF-β, MIG, HLA-DR, PAI-1, I-TAC, MMP-1, MMP-9, CD87 and Keratin 8/18
    (f) primary human umbilical artery smooth muscle cells in the presence of IL-4 and histamine with at least three different parameters selected from VCAM, CD40, HLA-DR, ICAM, IL-8, MCP-1, M-CSF, MIG, Thrombomodulin, and uPAR;
    (g) primary human umbilical artery smooth muscle cells in the presence of IL-1, TNF-α and IFNγ with at least three different parameters selected from VCAM, CD40, HLA-DR, ICAM, IL-8, MCP-1, M-CSF, MIG, Thrombomodulin, and uPAR;
    (h) human bronchial epithelial cells in the presence of IL-1β, TNFα and IFN-γ with at least three different parameters selected from ICAM-1, IL-1a, IP-10, TGF-β, MIG, HLA-DR, PAI-1, I-TAC, MMP-1, MMP-9, CD87 and Keratin 8/18;
    and (i) human bronchial epithelial cells in the presence of IL-4, IL-13 and TNFα with at least three different parameters selected from Eotaxin-3, ICAM-1, IL-1a, IL-8, TGF-β, PAI-1, MMP-9, uPA and Keratin 8/18;
    measuring changes in parameters as a result of introduction of said candidate agent in said at least three different parameters;
    deriving a biological dataset from said changes in parameters, wherein said biological dataset comprises control data from said asthma/atopy context system lacking said candidate agent;
    comparing said biological dataset to a reference biological dataset that includes predetermined agents that target specific asthma/atopy pathways to determine the presence of variation, wherein the presence or absence of variation from said reference biological datasets provides a characterization of said candidate agent's effect on allergic/atopic conditions.

2. The method according to claim 1, wherein said candidate agent is a polynucleotide or analog thereof.

3. The method according to claim 1, wherein said candidate agent is a drug or polypeptide.

4. A method for characterization of a candidate agent according to its effect on allergic/atopic conditions, the method comprising:
    contacting said candidate agent with a plurality of asthma/atopy context systems selected from
    (a) primary human umbilical vein endothelial cells (HUVEC) in the presence of IL-4 and histamine with at least three different cellular parameters selected from CD55, VCAM-1, P-selectin, Eotaxin-3, MCP-1, VEGF receptor 2 and uPAR (CD87);
    (b) HUVEC and T cells in the presence of IL-2 and superantigen with at least three different parameters selected from IFN-γ, TNF-alpha, IL-2, IL-4, IL-5, IL-8, IL10, IL-13, LT-alpha, CCR4, CCR5, CXCR3, IL-4Ralpha, CD11c, CD38, CD40, CD69, E-Selectin, Eotaxin-3, CD106, CD134, CD150, CD137, CD69, CD200, B7-H1, B7-H2, MIG and CD87;
    (c) Human neonatal fibroblasts (HDFn) in the presence of TNF, IL-1, IFN and TGFβ with at least three different parameters selected from ICAM, VCAM, CD40, CD90, IP-10, MCP-1, Collagen I, Mig, m-CSF, TIMP-2, PAI-I, and IL-8
    (d) HDFn in the presence of TGFβ with at least three different parameters selected from CD90, Collagen I, Collagen III, HLA-DR, PAI-I, and VCAM
    (e) human bronchial epithelial cells and HDFn in the presence of IL-4 and TNFα with, at least three different parameters selected from ICAM-1, IL-1a, IP-10, TGF-β, MIG, HLA-DR, PAI-1, I-TAC, MMP-1, MMP-9, CD87 and Keratin 8/18
    (f) primary human umbilical artery smooth muscle cells in the presence of IL-4 and histamine with at least three different parameters selected from VCAM, CD40, HLA-DR, ICAM, IL-8, MCP-1, M-CSF, MIG, Thrombomodulin, and uPAR;
    (g) primary human umbilical artery smooth muscle cells in the presence of IL-1, TNF-α and IFNγ with at least three different parameters selected from VCAM, CD40, HLA-DR, ICAM, IL-8, MCP-1, M-CSF, MIG, Thrombomodulin, and uPAR;

(h) human bronchial epithelial cells in the presence of IL-1β, TNFα and IFN-γ with at least three different parameters selected from ICAM-1, IL-1a, IP-10, TGF-β, MIG, HLA-DR, PAI-1, I-TAC, MMP-1, MMP-9, CD87 and Keratin 8/18;

and (i) human bronchial epithelial cells in the presence of IL-4, IL-13 and TNFα with at least three different parameters selected from Eotaxin-3, ICAM-1, IL-1a, IL-8, TGF-β, PAI-1, MMP-9, uPA and Keratin 8/18;

measuring changes in parameters as a result of introduction of said candidate agent in said at least three different parameters;

deriving a biological dataset from said changes in parameters, wherein said biological dataset comprises control data from asthma/atopy context systems lacking said candidate agent;

comparing said biological dataset to a reference biological dataset that includes predetermined agents that target specific asthma/atopy pathways to determine the presence of variation, wherein the presence or absence of variation from said reference biological datasets provides a characterization of said candidate agent's effect on allergic/atopic conditions.

5. A method for characterization of a candidate agent according to its effect on allergic/atopic conditions, the method comprising:

contacting said candidate agent with a plurality of asthma/atopy context systems selected from (a) primary human umbilical vein endothelial cells (HUVEC) in the presence of IL-4 and histamine with at least three different cellular parameters selected from CD55, VCAM-1, P-selectin, Eotaxin-3, MCP-1, VEGF receptor 2 and uPAR (CD87);

(b) HUVEC and T cells in the presence of IL-2 and superantigen with at least three different parameters selected from IFN-γ, TNF-alpha, IL-2, IL-4, IL-5, IL-8, IL10, IL-13, LT-alpha, CCR4, CCR5, CXCR3, IL-4Ralpha, CD11c, CD38, CD40, CD69, E-Selectin, Eotaxin-3, CD106, CD134, CD150, CD137, CD69, CD200, B7-H1, B7-H2, MIG and CD87;

(c) Human neonatal fibroblasts (HDFn) in the presence of TNF, IL-1, IFN and TGFβ with at least three different parameters selected from ICAM, VCAM, CD40, CD90, IP-10, MCP-1, Collagen I, Mig, m-CSF, TIMP-2, PAI-I, and IL-8

(d) HDFn in the presence of TGFβ with at least three different parameters selected from CD90, Collagen I, Collagen III, HLA-DR, PAI-I, and VCAM (e) human bronchial epithelial cells and HDFn in the presence of IL-4 and TNFα with at least three different parameters selected from ICAM-1, IL-1a, IP-10, TGF-β, MIG, HLA-DR, PAI-1, I-TAC, MMP-1, MMP-9, CD87 and Keratin 8/18

(f) primary human umbilical artery smooth muscle cells in the presence of IL-4 and histamine with at least three different parameters selected from VCAM, CD40, HLA-DR, ICAM, IL-8, MCP-1, M-CSF, MIG, Thrombomodulin, and uPAR;

(g) primary human umbilical artery smooth muscle cells in the presence of IL-1, TNF-α and IFNγ with at least three different parameters selected from VCAM, CD40, HLA-DR, ICAM, IL-8, MCP-1, M-CSF, MIG, Thrombomodulin, and uPAR;

(h) human bronchial epithelial cells in the presence of IL-β, TNFα and IFN-γ with at least three different parameters selected from ICAM-1, IL-1a, IP-10, TGF-β, MIG, HLA-DR, PAI-1, I-TAC, MMP-1, MMP-9, CD87 and Keratin 8/18;

and (i) human bronchial epithelial cells in the presence of IL-4, IL-13 and TNFα with at least three different parameters selected from Eotaxin-3, ICAM-1, IL-1a, IL-8, TGF-β, PAI-1, MMP-9, uPA and Keratin 8/18;

measuring changes in parameters as a result of introduction of said candidate agent in said at least three different parameters;

deriving a biological dataset from said changes in parameters, wherein said biological dataset comprises control data from said asthma/atopy context system lacking said candidate agent;

comparing said biological dataset to a reference biological dataset that includes predetermined agents that target specific asthma or atopy pathways to determine the presence of variation, wherein the presence or absence of variation from said reference biological datasets provides a characterization of said candidate agent's effect on allergic/atopic conditions wherein said plurality of systems are concatenated for simultaneous analysis.

* * * * *